United States Patent [19]

Bargain et al.

[11] 4,180,515

[45] Dec. 25, 1979

[54] ORGANOSILICON COMPOUNDS WITH FUNCTIONAL GROUPS

[75] Inventors: Michel Bargain, Lyon; Marcel Lefort, Caluire, both of France

[73] Assignee: Rhone-Poulenc Industries, Paris, France

[21] Appl. No.: 817,241

[22] Filed: Jul. 20, 1977

[30] Foreign Application Priority Data

Aug. 17, 1976 [FR] France .................................. 76 25534

[51] Int. Cl.² ............................................... C07F 7/08
[52] U.S. Cl. .......................................... 260/448.2 Q
[58] Field of Search ................................ 260/448.2 Q

[56] References Cited

U.S. PATENT DOCUMENTS

| | | | |
|---|---|---|---|
| 3,666,783 | 5/1972 | Lefort | 260/448.2 Q X |
| 3,994,947 | 11/1976 | Bond et al. | 260/448.2 Q |

*Primary Examiner*—Paul F. Shaver
*Attorney, Agent, or Firm*—Burns, Doane, Swecker & Mathis

[57] ABSTRACT

Novel organosilicon compounds containing various functional groups and processes for their preparation are disclosed. The compounds are silanes represented by the following general formula:

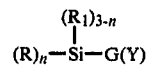

wherein R represents a hydrocarbon radical containing a carbon-carbon double bond; $R_1$ represents a hydrocarbon radical; G represents a divalent carbocyclic aromatic or heterocyclic radical; Y represents a group such as Cl, COCl, or COOH; and, n represents an integer equal to 1 or 2.

4 Claims, No Drawings

ORGANOSILICON COMPOUNDS WITH FUNCTIONAL GROUPS

BACKGROUND OF THE INVENTION

1. Field of the Invention

The present invention is directed to novel organosilicon compounds containing functional groups and the processes for preparing them.

2. Description of the Prior Art

The use of organosilicon compounds in preparing thermoplastic elastomers is well recognized in the art. Thus, in Belgian Patent Specification 834,046, published Mar. 30, 1976, polysiloxane thermoplastic elastomers are formed from recurrent groups of silicon bonded to oxygen upon which other functional groups may be attached to form complex, branched chain thermoplastic polymers.

SUMMARY OF THE INVENTION

The organosilicon compounds which are the subject of the present invention are represented by the following general formula:

In this formula (I), R represents a hydrocarbon radical containing a carbon-carbon double bond. $R_1$ represents a hydrocarbon radical. G represents a divalent carbocyclic aromatic or heterocyclic radical. Y represents a functional group such as Cl, COCl or COOH. Finally, n is an integer equal to 1 or 2.

According to a preferred embodiment, the organosilicon compounds have the general formula (I) pictured above, with slight changes in the appended groups. In this embodiment, R represents a monovalent hydrocarbon radical containing up to 10 carbon atoms and including a carbon-carbon double bond. $R_1$ represents a monovalent hydrocarbon radical selected from the group consisting of linear and branched alkyl radicals having up to 10 carbon atoms, cycloalkyl radicals having 3 to 6 carbon atoms in the ring, aryl radicals, cyano groups and halogen atoms. G represents a divalent carbocyclic aromatic or heterocyclic radical. These radicals may be mono- or polycyclic and, when polycyclic, may be condensed or joined by a simple bond, atom or group such as —$CH_2$—, —$C(CH_3)_2$—, O, $SO_2$, or CONH. The group represented by Y may be attached to any of the aromatic nuclei. Y represents a functional group selected from the group consisting of Cl, COOH, COOM (M representing an atom of sodium, potassium or lithium), $COOR_2$ and COCl, wherein $R_2$ represents a linear or branched alkyl radical having up to 4 carbon atoms. Finally, in this preferred embodiment, n represents an integer equal to 1 or 2 and when n is 2, the radicals represented by R may be different.

According to the most preferred embodiment, the symbols appended on formula (I) take on the following meaning: R represents a radical selected from the group consisting of vinyl, allyl, dichloro-2, 2-vinyl, butene-2 yl, propene-1 yl, butene-1 yl, methyl-2 and propene-1 yl; $R_1$ represents a radical selected from the group consisting of methyl, ethyl, trifluoro-4,4,4-butyl, phenyl, o-, m- or p-tolyl, xylyl, p- or m-chlorophenyl, dichloro-3,5 phenyl, trichlorophenyl, tetrachlorophenyl, β-cyanoethyl, γ-cyanopropyl; G represents one of the following radicals:

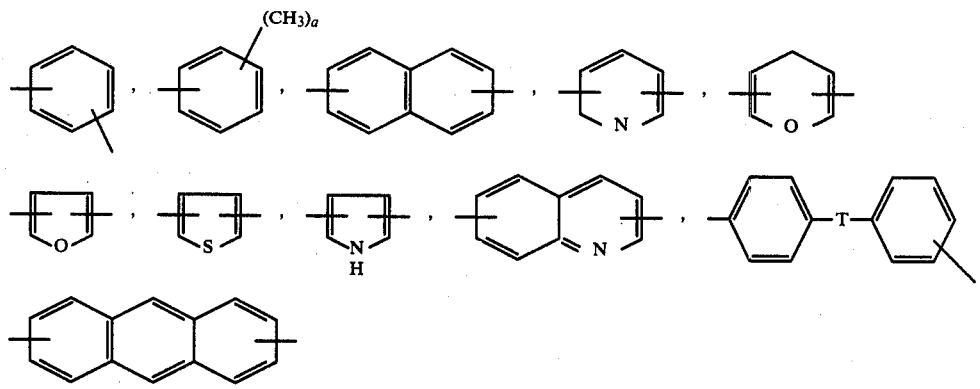

wherein a is an integer equal to 1 or 2 and T represents a simple bond or O, $CH_2$, $C(CH_3)_2$ or $SO_2$; n is an integer equal to 1.

Illustrative of the organosilicon compounds which are the subject of the present invention are:

—chloro-1 vinyldimethylsilyl-4 benzene
—vinyldimethylsilyl-4 benzoic acid
—chloro carbonyl-1 vinyldimethylsilyl-4 benzene
—divinylmethylsilyl-4 benzoic acid
—methoxycarbonyl-1 vinyldimethylsilyl-4 benzene
—ethoxycarbonyl-1 vinyldimethylsilyl-4 benzene
—ethoxycarbonyl-3 vinyldimethylsilyl-4 pyridine
—vinyldimethylsilyl-4 methoxycarbonyl-4' diphenylmethane
—vinyldimethylsilyl-4 methoxycarbonyl-4' diphenylether The compounds of formula (I) in which the symbol Y represents chlorine can be prepared via a method employing a Grignard reagent. According to this method, chlorosilane is reacted with Grignard reagent to attach the groups represented by G-Y and R to the silicon molecule. The order of attachment of these groups is not critical. Thus, either of the two procedures described below is operable.

Procedure 1

Step (a) Condensation of the Grignard reagent containing the radical represented by G with a dichlorinated silane to produce a dichlorosilane containing the radical G according to the following reaction scheme:

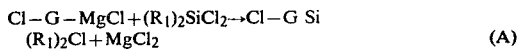

(A)

Step (b) Condensation of the product (A) with RMgCl to produce the desired organosilicon compound according to the following reaction scheme:

Procedure 2

Step (a) Condensation of RMgCl with a dichlorosilane according to the following reaction scheme:

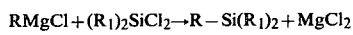
(B)

Step (b) Condensation of the product (B) with chlorinated Grignard reagent to produce the desired organosilicon compound via the following reaction sequence:
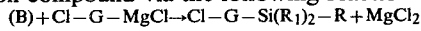

While the above procedures produce the organosilicon compounds of formula (I) in which n equals 1, it is understood that they may be applied with equal success to prepare the organosilicon compounds in which n equals 2.

Generally, the chlorinated organosilanes of the present invention are prepared at reaction temperatures between about 20° and 100° C. The reaction usually occurs in a diluted environment. However, when one of the reactants is itself a solvent, such as, dichlorobenzene, no other diluent or solvent is required. The choice of the solvent generally depends on the particular reactants. Thus, solvents which do not interfere with the Grignard reagent reactions are preferred. Examples of such solvents are linear or cyclic ethers, aromatic hydrocarbons and saturated linear or cyclic hydrocarbons.

The compounds of formula (I), in which Y represents a group other than chlorine, can be prepared from the chlorinated organosilanes of the present invention by conventional methods. For example, to form the compound of formula (I) in which Y is COOH, the chlorinated organosilane is reacted with Grignard reagent to form a complex with magnesium which is then reacted with an excess of $CO_2$ to achieve carbonation, followed by hydrolysis of the resulting product. Formula (I) compounds in which Y is $COOR_2$ or COOM are prepared from the carbonated product by conventional esterification or saponification reactions. Compounds of formula (I) in which Y represents COCl are produced by reacting the carboxylized derivatives with thionyl chloride or phosgene.

The compounds prepared in accordance with the present invention are useful because of the simultaneous presence in their molecule of an ethylene group and at least one other functional group. This feature allows addition of other constituents which may also contain functional groups. As a result, it is possible to form molecules containing many silicon atoms and functional groups. When the functional groups are carboxyl groups, the molecule may be polymerized by condensation to form polyesters, polyamides, polyurethanes and polyimides, as well as other types of thermoplastic elastomers. Conversely, the reactivity of the functional groups represented by Y in formula (I) may be utilized to initiate various reactions with other compounds.

The following examples are provided to further illustrate the present invention, it being understood that they are in no way intended to limit the scope of the invention.

EXAMPLE 1

Preparation of Dimethylvinyl P-chlorophenylsilane

Forty cubic centimeters (0.33 mol) of dimethyldichloro silane at 20° C. were placed in a 3-neck balloon-flask swept by a flow of nitrogen. Eighty cubic centimeters of toluene were added while shaking the mixture. The temperature was reduced to 5° C., then 0.33 mol of p-chlorophenylmagnesium chloride in 30 mn in the form of a solution in tetrahydrofurane (140 cubic centimeters) were added. Twenty cubic centimeters of toluene were added and the mixture was shaken for 2 hours 30 minutes. Then, 0.36 mol of vinylmagnesium chloride at 20 mn in the form of a solution in tetrahydrofurane (120 cubic centimeters) were added, the temperature being 25° C. at that time. Then the temperature of the reactive environment was changed and maintained for 2 hours. The reactive environment was cooled, the mixture was washed twice with 100 cubic centimeters of water, acidified with 5 cubic centimeters of HCl. Then, after decantation, the mixture was neutralized by means of sodium bicarbonate, dried, and 42 grams of a product containing (chromatography in the gaseous phase) 80 percent in terms of weight of p-chlorophenyldimethylvinylsilane (yield of 51.3 percent as compared to dimethylchlorosilane) was collected.

EXAMPLE 2

Twelve and one-half grams of chips of magnesium were placed in a 3-neck balloon-flask under a stream of nitrogen, 10 cubic centimeters of "magnesium compound a" (coming from a previous operation) was then poured in the mixture, was heated to 70° C., then 99 grams of dimethylvinylchlorophenylsilane were added, such as the one prepared in Example 1, in a solution with 150 cubic centimeters of THF. The flowing of chlorophenylsilane was completed in 2 hours. The mixture was kept boiling (reflux of tetrahydrofurane THF) for 12 hours in order to complete the reaction, then the environment containing p-(dimethylvinylsilylphenyl-magnesium chloride (a) was withdrawn. Two hundred cubic centimeters of THF were placed in a balloon-flask, and cooled by a bath of ice/acetone and saturated with $CO_2$ by splashing. Then the magnesium compound was poured in the flask while maintaining an excess of $CO_2$ and keeping the temperature of the reactive environment around 10° C. The reactive environment was then poured into two liters of ice water acidified by 55 cubic centimeters of a solution of HCl 10 N. Two hundred fifty cubic centimeters of toluene were added to promote decantation of the resulting paste.

After washing, treatment in a basic environment, precipitation, 62 grams of a white product was collected which had a melting point of 82° C. and was identified as being vinyldimethylsilyl-4 benzoic acid (yield of 61 percent as compared to dimethylvinyl chlorophenylsilane).

EXAMPLE 3

Preparation of Dimethylvinylsilyl-4 Benzoyl Chloride

Acid prepared in accordance with Example 2 was used.

This acid (815 grams=3.75 mol) was placed in a balloon-flask and heated at 90° C. The product became a pasty liquid while being shaken. Then, 595 grams (5 mols) of thionyl chloride were introduced into this environment for 1 hour and 30 minutes. The reaction was endothermic. The reactive environment was maintained at 45° C. for 1 hour and 20 minutes.

Dimethylvinylsilyl-4 benzoyl chloride was collected, the yield being 90.5 percent (as compared to dimethylvinylsilyl-4 benzoic acid). (Boiling point 98.5°–100° C. and pressure of 3 millimeters of mercury).

While the invention has now been described in terms of various preferred embodiments, the skilled artisan will readily appreciate that various substitutions, modifications, changes, and omissions, may be made without departing from the spirit thereof. Accordingly, it is intended that the scope of the present invention be limited solely by that of the following claims.

What is claimed is:

1. Organosilicon compounds corresponding to the general formula:

wherein R represents a monovalent aliphatic hydrocarbon or halocarbon radical having up to 10 carbon atoms and containing a carbon-carbon double bond; $R_1$ represents a member selected from the group consisting of a monovalent hydrocarbon radical having up to 10 carbon atoms and the halo and cyano derivatives thereof; G represents a divalent carbocyclic aromatic radical; Y represents a functional group selected from the group consisting of Cl, COOH, COOM, $COOR_2$ and COCl, in which M represents an atom of sodium, potassium or lithium and $R_2$ represents a linear or branched alkyl radical having up to 4 carbon atoms; and, n is an integer equal to 1 or 2.

2. The organosilicon compounds defined by claim 1, wherein n is equal to 1; R represents a radical selected from the group consisting of vinyl, allyl, dichloro-2,2 vinyl, trichloro-1,2,2 vinyl, butene-2 yl, propene-1 yl, butene-1 yl, methyl-2 and propene-1 yl; $R_1$ represents a radical selected from the group consisting of methyl, ethyl, trifluoro-4,4,4 butyl, phenyl, o-, m- or p-tolyl, xylyl, p- or m-chlorophenyl, dichloro-3,5 phenyl, trichlorophenyl, β-cyanoethyl and γ-cyanopropyl; and G represents a radical selected from the group consisting of:

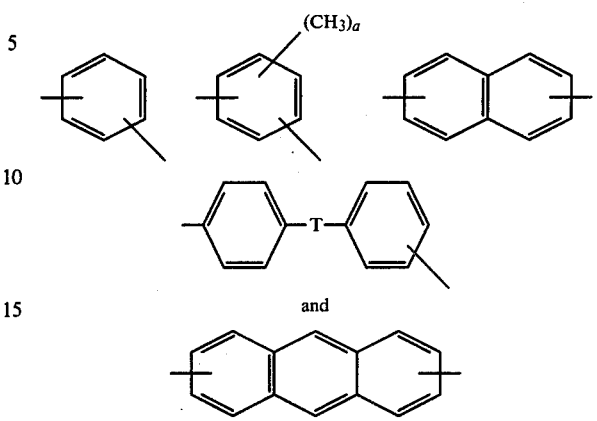

in which a is an integer equal to 1 or 2 and T represents a simple bond or a group selected from the group consisting of O, $CH_2$, $C(CH_3)_2$ and $SO_2$.

3. A process for the preparation of the organosilicon compounds defined by claim 1, comprising condensing Cl-G-MgCl with $(R_1)_2$-Si-$Cl_2$ to obtain Cl-G-Si$(R_1)_2$-Cl, and thereafter condensing the Cl-G-Si$(R_1)_2$-Cl with R-MgCl to obtain an organosilicon compound represented by the formula:

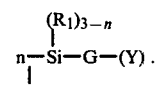

4. A process for the preparation of the organosilicon compounds defined by claim 1, comprising condensing R-MgCl with $(R_1)_2SiCl_2$ to produce R-Si$(R_1)_2$Cl and thereafter condensing the R-Si$(R_1)_2$Cl with Cl-G-MgCl to obtain an organosilicon compound represented by the formula:

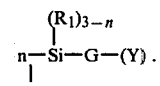

* * * * *